(12) United States Patent
Chuter et al.

(10) Patent No.: US 9,370,437 B2
(45) Date of Patent: Jun. 21, 2016

(54) STENT HAVING LESS INVASIVE ENDS

(75) Inventors: Timothy A. M. Chuter, San Francisco, CA (US); William K. Dierking, West Lafayette, IN (US); Alan R. Leewood, Lafayette, IN (US); Blayne A. Roeder, Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 1539 days.

(21) Appl. No.: 12/338,020

(22) Filed: Dec. 18, 2008

(65) Prior Publication Data

US 2009/0171438 A1 Jul. 2, 2009

Related U.S. Application Data

(60) Provisional application No. 61/016,731, filed on Dec. 26, 2007.

(51) Int. Cl.
*A61F 2/915* (2013.01)
*A61F 2/90* (2013.01)
*A61F 2/07* (2013.01)
*A61F 2/848* (2013.01)

(52) U.S. Cl.
CPC . *A61F 2/915* (2013.01); *A61F 2/90* (2013.01); *A61F 2002/075* (2013.01); *A61F 2002/8483* (2013.01); *A61F 2002/91558* (2013.01); *A61F 2220/0016* (2013.01); *A61F 2220/0075* (2013.01); *A61F 2250/0036* (2013.01)

(58) Field of Classification Search
CPC .............. A61F 2/82; A61F 2/86; A61F 2/89; A61F 2/844; A61F 2002/825; A61F 2250/0036; A61F 2/915
USPC .......................................... 623/1.15, 1.3, 1.36
See application file for complete search history.

(56) References Cited

U.S. PATENT DOCUMENTS

| | | | |
|---|---|---|---|
| 5,135,536 A | 8/1992 | Hillstead | |
| 5,907,893 A | 6/1999 | Zadno-Azizi et al. | |
| 5,922,020 A * | 7/1999 | Klein et al. | 623/1.15 |
| 6,042,606 A | 3/2000 | Frantzen | |
| 6,245,101 B1 | 6/2001 | Drasler et al. | |
| 6,312,460 B2 | 11/2001 | Drasler et al. | |
| 6,416,543 B1 | 7/2002 | Hilaire et al. | |
| 6,475,237 B2 | 11/2002 | Drasler et al. | |
| 6,540,774 B1 | 4/2003 | Cox | |
| 6,579,310 B1 * | 6/2003 | Cox et al. | 623/1.16 |
| 6,896,696 B2 | 5/2005 | Doran et al. | |
| 7,135,038 B1 | 11/2006 | Limon | |
| 2003/0120338 A1* | 6/2003 | Chobotov et al. | 623/1.36 |
| 2003/0125802 A1 | 7/2003 | Callol et al. | |
| 2003/0176912 A1 | 9/2003 | Chuter et al. | |
| 2005/0159803 A1* | 7/2005 | Lad et al. | 623/1.13 |
| 2006/0161243 A1 | 7/2006 | Fearnot et al. | |
| 2006/0265050 A1 | 11/2006 | Morris et al. | |
| 2006/0287707 A1 | 12/2006 | Roeder et al. | |
| 2007/0021824 A1 | 1/2007 | Roeder et al. | |
| 2008/0051876 A1* | 2/2008 | Ta et al. | 623/1.16 |

* cited by examiner

*Primary Examiner* — Howie Matthews
(74) *Attorney, Agent, or Firm* — Brinks Gilson & Lione

(57) ABSTRACT

The present examples provide a stent for use in a medical procedure that comprises at least one apex having first and second generally straight portions and a curved portion disposed between the first and second straight portions. The curved portion may comprise at least one region having a cross-sectional area that is less than a cross-sectional area of the first and second straight portions, which may facilitate compression of the stent and insertion of the stent into smaller vessels. The stent may be used alone, or in conjunction with a stent-graft, and may comprise one or more barbs configured to engage an inner wall of a vessel or duct.

20 Claims, 5 Drawing Sheets

STENT HAVING LESS INVASIVE ENDS

PRIORITY CLAIM

This invention claims the benefit of priority of U.S. Provisional Application Ser. No. 61/016,731 entitled "Stent Having Less Invasive Ends," filed Dec. 26, 2007, the disclosure of which is hereby incorporated by reference in its entirety.

BACKGROUND

The present invention relates generally to apparatus and methods for treating medical conditions, and more specifically, to stents for use in body vessels to treat those medical conditions.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

With balloon-expandable stents, the stent may be delivered and deployed using a catheter having proximal and distal ends and one or more balloons disposed on the catheter. The stent may be coupled to the balloon during insertion until the target site is reached, and then deployed by inflating the balloon to expand the stent to bring the stent into engagement with the target site. Alternatively, the stent may be placed separately in the vessel and a subsequent catheter having an expansion portion may then be inserted into the stent to expand the stent at the target site.

Various existing self-expanding and balloon-expandable stent designs and configurations comprise end regions including one or more apices. The apices commonly comprise relatively acute bends or present somewhat pointed surfaces, which may facilitate compression of the stent to a relatively small delivery profile due to the tight bend of the apices. Although having this advantage, in some situations, such relatively acute or pointed apices may be undesirable.

For example, in the case of a suprarenal attachment stent employed during treatment of an abdominal aortic aneurysm, the stent may have one end coupled to a graft material and the other end engage a healthy portion of a vessel wall. If the acute bends of the apices that engage the graft material are too pointed, sharp or otherwise invasive, then it may adversely impact or abrade the graft material, leading to breakdown of, or leakage through, the graft material. Similarly, if the ends of the stent that engage the vessel wall are too pointed, sharp or otherwise invasive, then it may have an adverse effect upon the vessel wall in the expanded state.

Certain existing stents comprise relatively round, or arcuate, proximal and distal apices, as opposed to relatively pointed or acute apices. The provision of such rounded apices at the distal and proximal ends of the stent may be less invasive upon graft material and/or vessel walls. However, where stents comprise well-rounded apices in the expanded state, compression of the stent, and in particular the apices, may be limited and the stent may not be suitable for delivery into smaller vessels. There is a need for smaller profile delivery and stent-graft systems that can be used in smaller vessels, such as those present in women and other populations.

In view of the above, it would be desirable to provide a stent having at least one relatively rounded apex that is less invasive in an expanded state, and further having the ability to be compressed to a relatively low delivery profile.

SUMMARY

The present embodiments provide a stent having at least one apex comprising first and second generally straight portions and a curved portion disposed between the first and second straight portions. The curved portion of the stent comprises at least one region in which the stent material in that region has a cross-sectional area that is less than a cross-sectional area of the stent material in the first and second straight portions. The reduced area of the stent material in the curved portion may facilitate or improve the overall compression of the stent to a relatively low profile delivery configuration.

In one example, the stent comprises a substantially uniform taper formed between the first straight portion of the stent and a midpoint of the curved portion, and further may comprise a substantially uniform taper between the second straight portion and the midpoint. Here, the midpoint may comprise the smallest cross-sectional area of any point along the curved portion. Alternatively, the first and second straight portions may taper toward the curved portion to a smaller diameter, and the curved portion may maintain that smaller diameter throughout the curved portion.

In another example, the stent cross-section may comprise a variable taper formed along at least a portion of the curved portion, thereby forming one or more regions along the curved portion having a reduced cross-sectional area relative to the first and second straight portions.

The stent comprises expanded and compressed states. In the expanded state, the curved portion of the stent may comprise a generally arcuate shape. When compressed, at least a portion of the curved portion may straighten, overlap, or impinge with itself to reduce the radial profile of the apex. Advantageously, the one or more apices may be relatively rounded or arcuate in an expanded shape, yet comprise a relatively small delivery profile in a compressed state.

The stent may comprise multiple proximal apices and multiple distal apices. Each proximal apex may be integrally formed with the next adjacent proximal apex, and each distal apex may be integrally formed with the next adjacent distal apex. For example, each of the proximal apices may be circumferentially offset from the distal apices. Further, the stent may comprise at least one strut segment disposed between a proximal apex and a distal apex, where the strut segment is angled with respect to a longitudinal axis of the stent in an expanded state. In one example, a strut segment is integral with one strut of a proximal apex and one strut of a distal apex.

A stent as described may be used alone or in conjunction with a stent-graft. The stent may be coupled to the proximal end of a graft and used, for example, as an attachment stent for endovascular graft fixation. Alternatively, the stent may be one component of a stent-graft, in which the stent overlaps with the graft material either internally or externally to the graft material. The stent may additionally comprise one or more barbs formed integrally with the stent and configured to engage an inner wall of a vessel or duct. For example, an integral barb may be formed at the juncture of one apex to the next adjacent connected apex.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Figure 1:
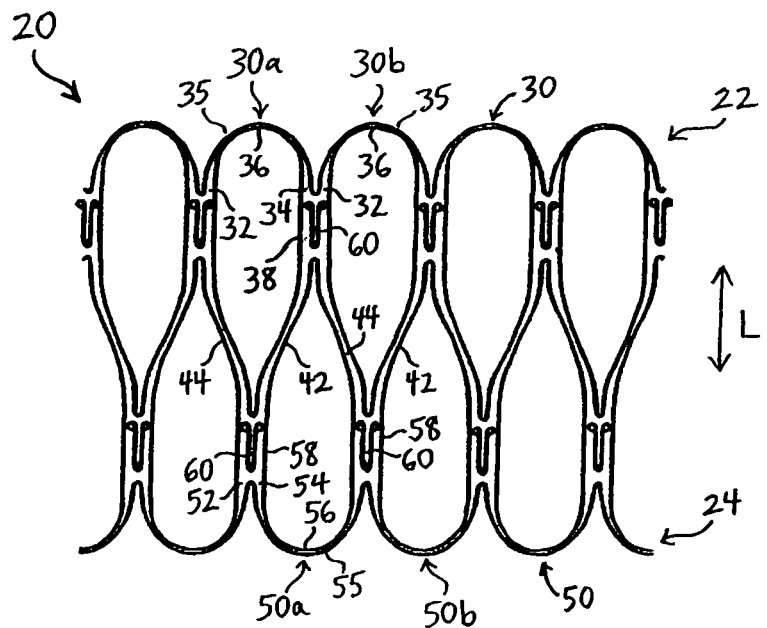
FIG. 1 is a top view of a portion of a stent.

Referring now to FIG. 1, a portion of a stent 20 provided in accordance with a first example is described. The stent 20 generally comprises a proximal stent end 22 and a distal stent end 24. While the stent 20 is depicted as being flat, the stent may form a generally circular configuration or could be circumferentially wound in a continuous fashion to form a coil or helical type structure.

The stent 20 has a reduced diameter delivery state so that it may be advanced to a target location within a vessel or duct. The stent 20 also has an expanded deployed state to apply a radially outward force upon at least a portion of a vessel or duct, e.g., to maintain patency within a passageway, or to hold open the lumen of a graft. In the expanded state, fluid flow is allowed through a central lumen of the stent 20.

As shown in FIG. 1, the stent 20 may comprise at least one generally arcuate apex, and preferably comprises a series of arcuate, adjacent apices. As shown, adjacent apices may abut each other and also may be attached to each other or formed integrally. As shown in FIG. 1, the proximal end 22 of the stent 20 may comprise multiple adjacent proximal apices 30a and 30b, while the distal end 24 of the stent 20 may comprise multiple adjacent distal apices 50a and 50b, where the apices of the proximal end are offset from the apices of the distal end. As shown here, the apices 30 located at the proximal end 22 are symmetrical to the apices 50 located at the distal end 24.

Figure 2A:
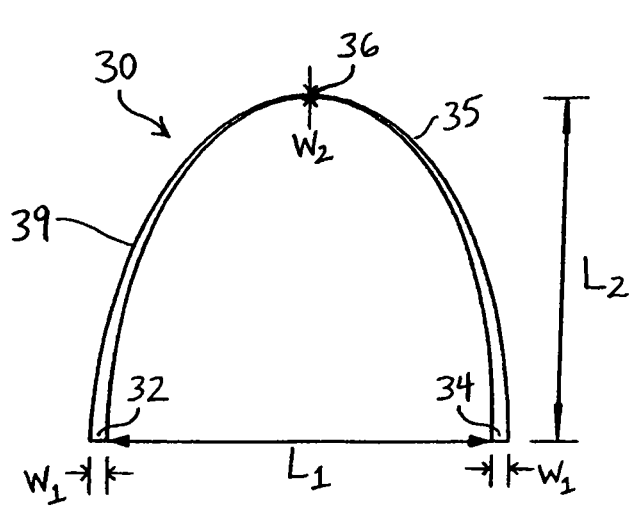
FIG. 2A is a top view of an apex of the stent of FIG. 1.

Referring now to FIG. 2A, features associated with an individual, exemplary apex 30 are shown. As shown, the apex 30 may include first and second generally straight portions 32 and 34 and a curved portion 35 formed between the straight portions. As used in the present application, the term "generally straight" refers to having a portion aligned with a longitudinal axis L of the stent 20, as shown in FIG. 1. Accordingly, the first and second straight portions 32 and 34 generally are parallel with respect to the longitudinal axis L of the stent 20. Further, the term "curved portion" refers generally to the entire surface of the stent 20 that is disposed between the first and second generally straight portions 32 and 34. Therefore, as shown in FIGS. 1-2A, the curved portion 35 comprises a generally arcuate shape and spans approximately 180 degrees between the first and second generally straight portions 32 and 34.

The curved portion 35 of the stent 20 may include at least one region having a cross-sectional area that is less than a cross-sectional area of the first and second straight portions 32 and 34. For example, the curved portion 35 may have a midpoint 36 having a cross-sectional width $w_2$, as shown in FIG. 2C, which is less than a cross-sectional width $w_1$ of the first and second straight portions 32 and 34, as shown in FIG. 2B.

Figure 2B:
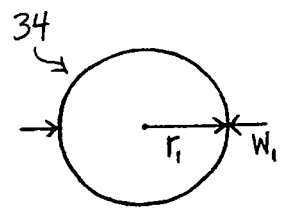
FIG. 2B is a cross-sectional view of a straight portion of the stent of FIG. 2A.
Figure 2C:
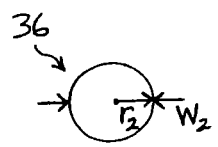
FIG. 2C is a cross-sectional view of a curved portion of the stent of FIG. 2A.

In the embodiment of FIG. 2A, the cross-sectional width $w_1$ is approximately equal to the diameter at some point along the first and second straight portions 32 and 34, and therefore, the width $w_1$ is approximately twice the length of the radius $r_1$, as shown in FIG. 2B. Therefore, the cross-sectional area of the first and second straight portions 32 and 34 may be calculated as $A_1=(\pi)(r_1^2)$. Similarly, the cross-sectional area at the midpoint 36 may be calculated as $A_2=(\pi)(r_2^2)$. Since the cross-sectional width $w_1$ of the first and second straight portions 32 and 34 is larger than the cross-sectional width $w_2$ of the midpoint 36, the cross-sectional area $A_1$ of the first and second straight portions 32 and 34 will be larger than the cross-sectional area $A_2$ of the midpoint 36 of the curved portion 35.

Figure 7:
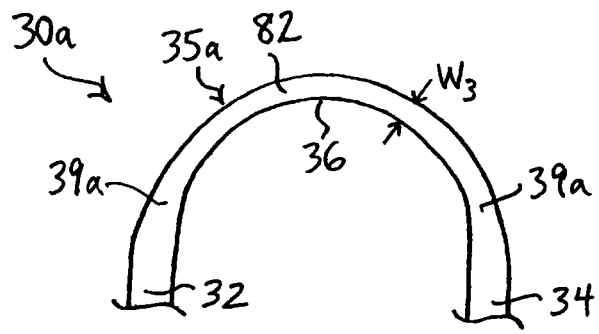
FIG. 7 is a top view of a stent apex.
Figure 8:
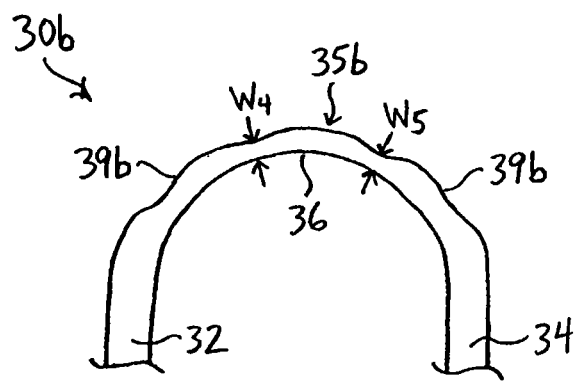
FIG. 8 is a top view of another stent apex.

As shown in FIG. 2A, since there is a uniformly reduced taper throughout the curved portion 35, culminating at the midpoint 36, each location along the curved portion 35 comprises a cross-sectional area that is less than the cross-sectional areas of the first and second straight portions 32 and 34. However, as explained in FIG. 7 below, the taper does not have to culminate at midpoint 36, as the straight portions 32 and 34 may taper into a part of the curved portion 35 and then the curved portion 35 may have a uniform cross-section smaller than the cross-sections of the straight portions 32, 34. Moreover, not all locations along the curved portion 35 need to have a cross-sectional area that is less than the cross-sectional areas of the first and second straight portions 32 and 34, as depicted in FIG. 8 below.

Struts of the stent 20 may comprise a substantially flat wire profile or may comprise a rounded profile. Regardless of whether the stent is a flat or rounded wire, the curved portion 35 has at least one region having a cross-sectional area that is less than a cross-sectional area of the first and second straight portions 32 and 34. While the cross-sectional areas of the first and second straight portions 32 and 34 preferably are identical, it is not required.

Referring still to FIG. 2A, an inner surface of the first straight portion 32 may be spaced apart from an inner surface of the second straight portion 34 by a longitudinal length $L_1$. For example, the longitudinal length $L_1$ may be from about 8.5 to about 9.0 mm. Additionally, a longitudinal length $L_2$ may be used to define the distance between an inner surface of the midpoint 36 of the apex 30, and the beginning of first and second straight segments 32 and 34, i.e., where the curved portion 35 terminates. For example, the longitudinal length $L_2$ may be from about 4.5 to about 4.7 mm.

Further, cross-sectional widths of struts of the first and second straight portions 32 and 34 may range from about 0.7 to about 0.9 mm, and more preferably from about 0.8 mm. By contrast, a cross-sectional width of a strut at the midpoint 36 of the curved portion 35 may be about 0.05 mm. As noted above, these cross-sectional widths may directly correspond to the cross-sectional areas. Therefore, in the example of FIGS. 2A-2C, the cross-sectional width $w_1$ may be about 16 times greater than the cross-sectional width $w_2$. As explained further with respect to FIGS. 7-9 below, the cross-sectional width $w_1$ may be only slightly greater than the cross-sectional width $w_2$ at the midpoint 36, for example, less than twice the area.

In order to transition between the cross-sectional widths $w_1$ of the first and second straight portions 32 and 34 and the reduced cross-sectional width $w_2$ of the curved portion, at least one taper is provided. As shown in FIG. 2A, a substantially uniform taper 39 is provided between the first straight portion 32 and the midpoint 36, and an opposing substantially uniform taper is provided between the second straight portion 34 and the midpoint 36. Accordingly, a gradual decline in cross-sectional area is provided between the first and second straight portions 32 and 34 and the midpoint 36 of the curved portion 35. However, the taper through the curved portion 35 need not continue to the midpoint 36. As generally shown in FIG. 7 below, the taper may level out at some point just prior to, or into, the curved portion, thereby leaving the curved portion at a constant width or diameter that is less than the width or diameter of the straight portions.

As explained in further detail below, the provision of generally arcuate apices having at least one region along the curved portion 35 with a smaller cross-sectional area, relative to the straight portions 32 and 34, may reduce the overall delivery profile of the stent 20. This may allow the stent 20 to be delivered into smaller vessels and/or more tortuous vasculature, as explained further below.

Referring still to FIG. 1, adjacent apices 30a and 30b at the proximal end 22 of the stent 20 may meet with one another to form a proximal transition region 38. As shown in FIG. 1, a first straight portion 32 of the apex 30b meets up with a second straight portion 34 of the apex 30a, thereby forming the proximal transition region 38. Therefore, the proximal transition region 38 comprises a larger cross-sectional area relative to the apices of the stent 20. Like the first and second straight portions 32 and 34, the proximal transition region 38 is generally straight, or parallel, with respect to the longitudinal axis L of the stent 20, as shown in FIG. 1.

Figure 3:
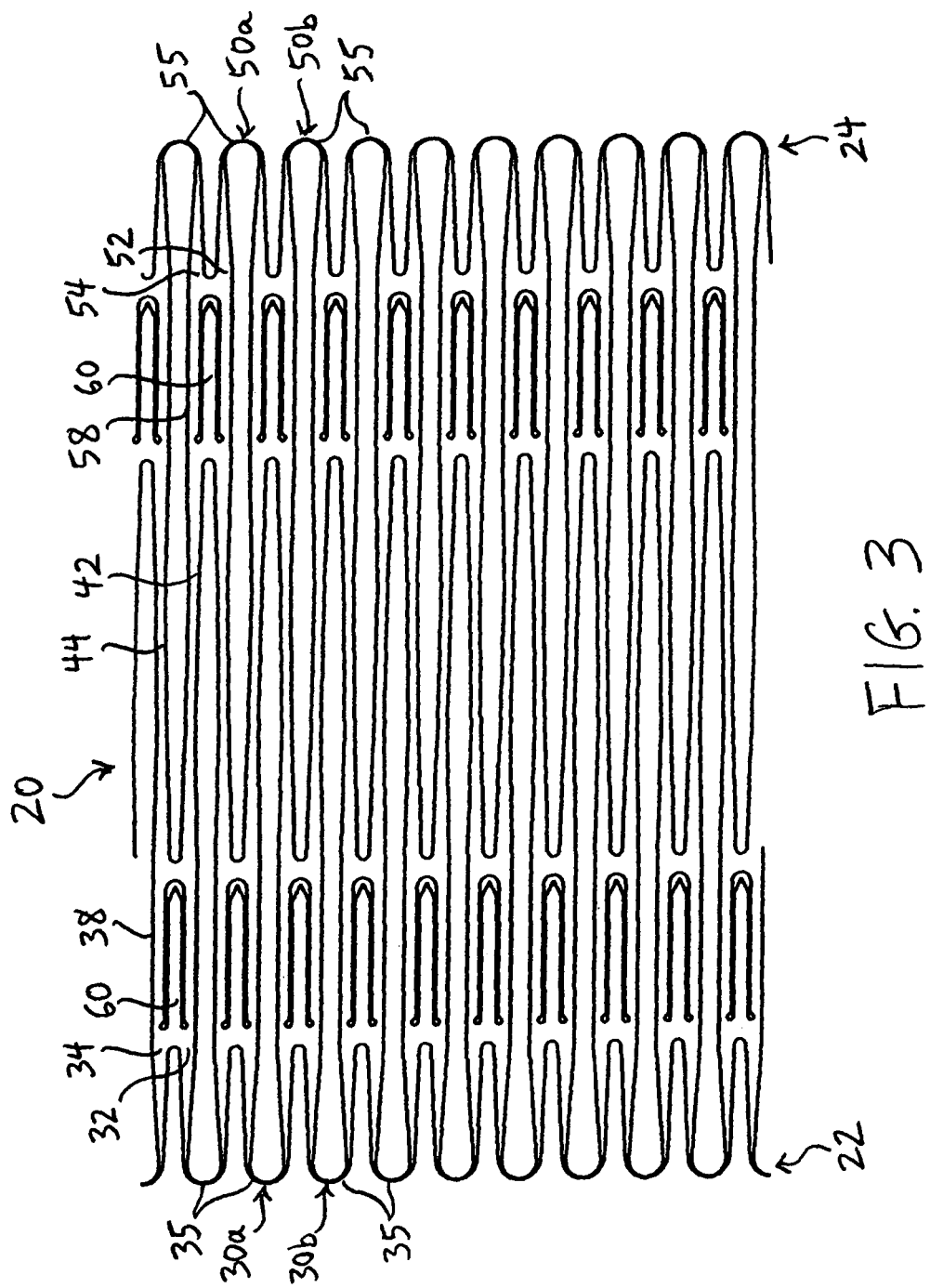
FIG. 3 is a top view of a portion of the stent of FIG. 1 in a compressed or partially compressed state.

The proximal transition region 38 extends distally and splits into first and second angled strut segments 42 and 44, respectively. In a compressed state, the first and second angled strut segments 42 and 44 may be compressed such that they are substantially parallel to one another, as depicted in FIG. 3 below. In the expanded state shown in FIG. 1, the first and second angled strut segments 42 and 44 are disposed an angle relative to the first and second straight portions 32 and 34 and the longitudinal axis L of the stent 20. In the expanded state, the first and second angled strut segments 42 and 44 may be disposed at an angle of about 15-45 degrees relative to the longitudinal axis L of the stent 20, and more preferably, at an angle of about 30 degrees, as depicted in FIG. 1.

The first and second angled strut segments 42 and 44 extend from the proximal transition region 38 in a generally V-shaped manner towards the distal end 24 of the stent 20, as shown in FIG. 1. Each first angled strut segment 42 unites with an adjacent second angled strut segment 44 to form a distal transition region 58. As shown in FIG. 1, the distal transition region 58 then divides into first and second straight portions 52 and 54 to form a series of distal apices 50 at the distal end 24 of the stent 20. Curved portions 55, which preferably are symmetrical to the curved portions 35 described above, are disposed between the first and second straight portions 52 and 54. In this manner, a series of distal apices 50a and 50b are formed.

As shown in FIG. 1, each of the proximal and distal apices may be integrally formed with the next adjacent apex. Specifically, proximal apex 30a is integrally formed with adjacent proximal apex 30b, and similarly, distal apex 50a is integrally formed with adjacent distal apex 50b. In this manner, the stent 20 may be formed into a continuous, generally cylindrical shape. It may be noted that the each of the proximal apices are circumferentially offset from the distal apices, i.e., when the stent is cylindrically formed, the proximal apex 30a is circumferentially offset from the distal apex 50a, which in turn is offset from the next adjacent proximal apex 30b, as shown in FIG. 1.

Expansion of the stent 20 is at least partly provided by the angled strut segments 42 and 44, which may be substantially parallel to one another in a compressed state, but may tend to bow outward away from one another in the expanded state shown in FIG. 1. As explained further below, the stent 20 may be formed from any suitable material, and preferably nitinol. If manufactured from nitinol, the stent 20 may assume the expanded state shown in FIG. 1 upon removal of a delivery sheath.

Figure 11:
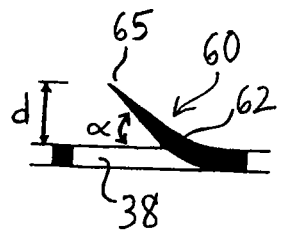
FIG. 11 is a side view of a barb that may be used in conjunction with the stents described herein.

Referring now to FIG. 1 and FIG. 11, the stent 20 may comprise at least one barb 60. The barb 60 may be integrally, as part of the strut, formed with the stent 20, or may comprise an external barb that is adhered to a surface of a strut of the stent 20. Preferably, as shown in FIG. 1, multiple integral barbs 60 are provided. The barbs 60 may be formed by laser cutting a desired barb shape into the proximal transition region 38 and/or the distal transition region 58. Since the transition regions may comprise an increased width relative to other regions of the stent 20, it may be easier to perforate portions of the transition regions without adversely affecting the structural integrity of the stent.

Once the desired barb shape is cut, a main body 62 of the barb 60 may be bent in an outward direction, as shown in FIG. 11. The main body may be bent outward an angle α with respect to an upper surface of the transition region 38. The angle α may comprise any acute angle, or alternatively may be substantially orthogonal or obtuse. For example, the angle α is about 5 to 45 degrees. In the bent state, a distance d between the upper surface of the transition region 38 and the tip 65 of the barb 60 may be about 1.0 mm. If desired, barb 20 may be sharpened, for example, by grinding the tip 65, to facilitate engagement at the target site.

Referring to FIG. 3, the stent 20 is shown in a compressed or partially compressed state. As shown, the angled strut segments 42 and 44 preferably are substantially parallel to one another in the compressed or partially compressed state. With previously known stents having well-rounded apices, the overall compression of the stent may be limited by the configuration of the rounded apices and/or the inherent material properties of the stent. Advantageously, since the present examples employ curved portions 35 and 55 that comprise one or more regions having a reduced cross-sectional area, further compression of the stent 20 may be achieved, as explained further with respect to FIGS. 4-6 below.

Figure 6:
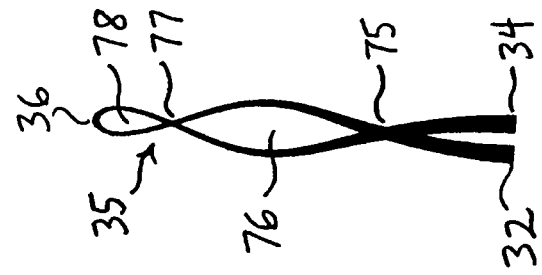
FIGS. 4-6 are top views illustrating compression of an apex of the stent of FIG. 1.
Figure 5:
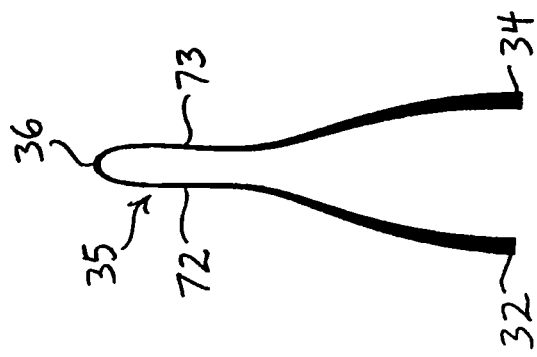
Figure 4:
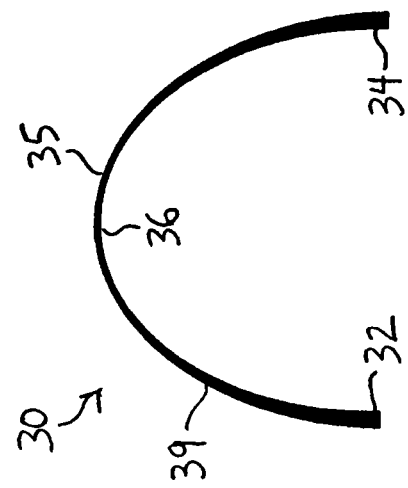

Referring now to FIGS. 4-6, in order to achieve further overall compression of the stent 20, the curved portions 35 of the proximal apices 30, as well as the curved portions 55 of the distal apices 50, may undergo further compression. FIGS. 4-6 show a sequence of compression in addition to, or in lieu of, the compression shown in FIG. 3.

In FIG. 4, the proximal apex 30 is shown in an expanded state. In FIG. 5, the proximal apex 30 is shown in a partially compressed state. Since the curved portion 35 comprises a region having a reduced cross-sectional area, it may be inclined to compress further, for example, by forming two substantially parallel segments 72 and 73 surrounding the midpoint 36. Then, in a fully compressed state, shown in FIG. 6, at least a portion of the curved portion 35 may overlap with itself. In the fully compressed state, the curved portion 35 may overlap with itself at one or more locations 75 and 77, thereby forming open spaces 76 and 78. The curved portion also may impinge upon itself in the fully compressed state.

Advantageously, the profile of the apex 30 in the compressed state may be considerably less than the profile of the apex in the expanded state. By reducing a cross-sectional area along at least one region of the curved portion 35, straightening, overlapping and/or impinging of the curved portion 35 may be achieved upon compression, which may reduce the delivery profile of the proximal and distal apices 30 and 50. Therefore, the overall delivery profile of the stent 20 may be reduced, facilitating insertion of the stent 20 into smaller vessels and through tortuous vasculature.

In other examples, the apices 30 and 50 may not overlap into the form shown in FIG. 6. Rather, in some cases, portions of the curved portion 35 on opposing sides of the midpoint 35 may abut, or be disposed adjacent to one another. In each instance, the provision of one or more regions having a reduced cross-sectional area along a portion of the curved portion 35 may facilitate compression of the stent 20 to a smaller delivery profile.

The stent 20 may be manufactured from a super-elastic material. Solely by way of example, the super-elastic material may comprise a shape-memory alloy, such as a nickel titanium alloy (nitinol). When the nitinol strut that forms the curved portion 35 is transformed between the expanded state of FIG. 4 and the fully compressed state of FIG. 6, an overall strain imposed upon the curved portion 35 should not exceed about 10-12%. In one example, the strain imposed upon the curved portion 35 will not exceed about 8%. If the strain imposed upon nitinol exceeds about 10-12%, then the stent compression may induce a permanent strain on the material and the apex might not return to its intended expanded configuration upon removal from a delivery sheath, or the long-term durability of the stent may be compromised. Based on analytical modeling, the tapered shape of the curved portion 35, as shown in FIGS. 4-6, will not exceed about 10-12% if manufactured from a super-elastic material, such as nitinol, and therefore will return to its original shape upon removal from a delivery sheath.

Alternatively, the stent 20 may be made from other metals and alloys that allow the stent 20 to return to its original, expanded configuration upon deployment, without inducing a permanent strain on the material due to compression. Solely by way of example, the stent 20 may comprise other materials such as stainless steel, cobalt-chrome alloys, amorphous metals, tantalum, platinum, gold and titanium. The stent 20 also may be made from non-metallic materials, such as thermoplastics and other polymers.

Figure 9:
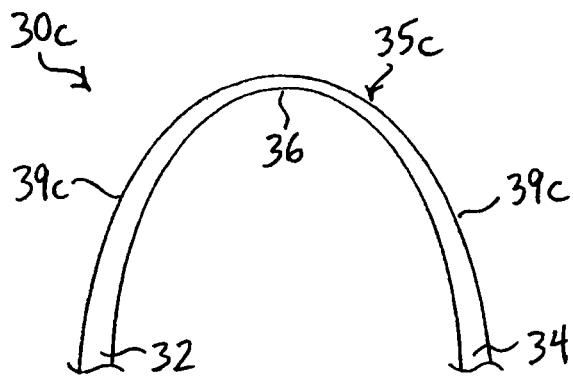
FIG. 9 is a top view of another stent apex.

Referring now to FIGS. 7-9, various configurations of apices are described. In each instance, the cross-sectional widths $w_1$ of the first and second straight portions 32 and 34 are greater than the cross-sectional widths of at least one region of the curved portions 35a-35c. Therefore, if the struts are substantially rounded, the cross-sectional areas $A_1$ of the first and second straight portions 32 and 34 will be greater than the cross-sectional areas $A_1$ of the curved portions 35a-35c, as generally explained above.

Referring to FIG. 7, apex 30a comprises a curved portion 35a having an arcuate segment 82. Opposing tapers 39a are disposed between the arcuate segment 82 and the first and second straight portions 32 and 34. In this example, the cross-sectional widths $w_1$ of the first and second straight portions 32 and 34 are greater than the cross-sectional width $w_3$ of the arcuate segment 82 of the curved portion 35a. It should be noted that the tapers 39a are not continuous along the entire length of the curved portion 35a. Rather, the arcuate segment 82 comprises a continuous cross-sectional width $w_3$ that is smaller than the cross-sectional widths $w_1$ of the first and second straight portions 32 and 34.

Referring to FIG. 8, apex 30b comprises one or more staged or variable tapers 39b that are provided along one or more regions of the curved portion 35b. In the example of FIG. 8, multiple tapers 39b are provided that variably reduce the cross-sectional area of regions of the curved portion 35b to dimensions less than the cross-sectional areas of the first and second straight portions 32 and 34. More specifically, the curved portion 35b comprises cross-sectional widths $w_4$ and $w_5$, each of which are smaller than the cross-sectional widths $w_1$ of the first and second straight portions 32 and 34. Therefore, the curved portion 35b may comprise cross-sectional areas that are smaller than the cross-sectional areas of the first and second straight portions 32 and 34. It should be noted that the midpoint 36 therefore does not need to comprise the smallest cross-sectional area in each example. During compression of the apex 30b, the regions of the curved portion 35b that comprise smaller cross-sectional widths $w_4$ and $w_5$ may promote overlapping or otherwise serve to compress the apex 30b to a smaller profile.

Referring to FIG. 9, apex 30c comprises a curved portion 35c having a substantially uniform taper 39c between the first and second straight portions 32 and 34 and the midpoint 36. Here, the apex 30c is substantially arch-shaped and the cross-sectional widths $w_1$ of the first and second straight portions 32 and 34 are always greater than the cross-sectional width along any region of the curved portion 35c.

Advantageously, in each of the foregoing examples, the relatively well-rounded curvature provided by outer surfaces of the apices 30a-30c may be less invasive upon a vessel when deployed. Further, the reduced cross-sectional area along at least one region of the curved portions 35a-35c may facilitate and enhance compression of the apices 30a-30c, and therefore the stent 20 may be reduced to a smaller overall delivery profile.

Figure 10:
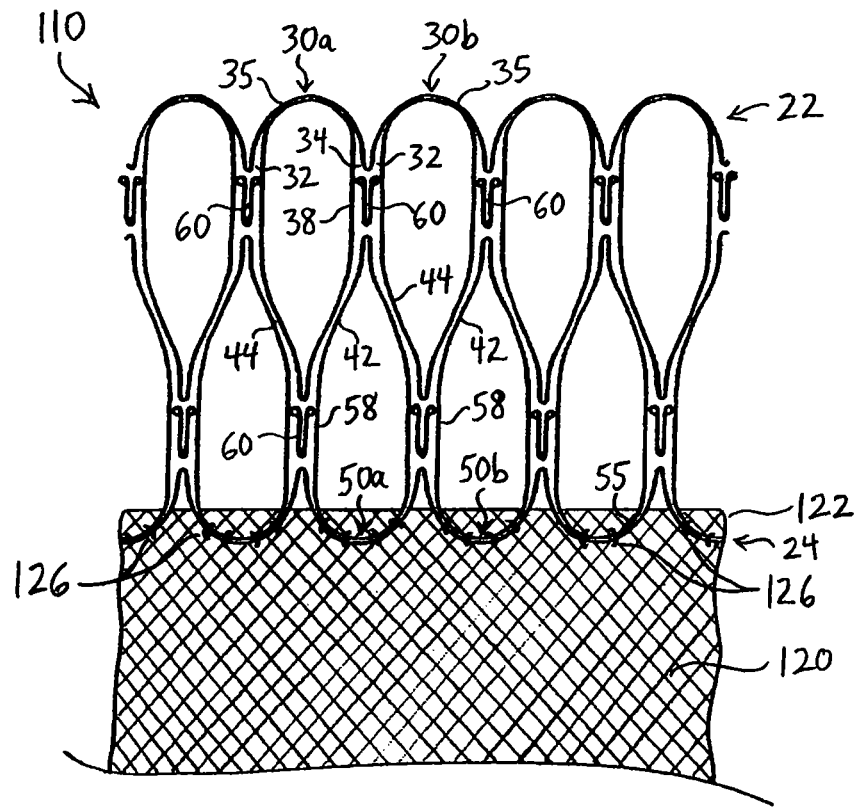
FIG. 10 is a top view showing a portion of the stent of FIG. 1 coupled to an end region of a graft.

Referring now to FIG. 10, the stent 20 may be coupled to a portion of graft material to form a stent-graft 110. For example, as shown in FIG. 10, the stent 20 may be used as an attachment stent for endovascular graft fixation. The stent 20 of FIG. 1 may be coupled to a proximal end 122 of a graft 120. The graft 120 may overlap with an aneurysm to seal off fluid flow into the aneurysm, while the proximal end 22 of the stent 20 may extend in a proximal direction away from the graft 120, e.g., to engage a healthy portion of a vessel wall away from a diseased portion of the aneurysm.

During manufacture, the apices 50 at the distal end 24 of the stent 20 may be coupled to the graft 120, for example, using one or more sutures 126. In one example, multiple sutures are looped through the graft 120 around the curved portions 55. While four sutures are illustratively depicted for multiple apices 50, at least one other distal apex 50 is attached to the graft 120 using only two sutures. Alternatively, any number of sutures may be employed, ranging from one suture per apex to more than four sutures per apex.

Advantageously, since the curved portions 55 comprise a generally arcuate shape, an increased suture attachment zone may be provided over approximately 180 degrees, thereby allowing for the provision of a greater number of sutures and enhanced coupling between the stent 20 and the graft 120. Moreover, since the end regions of the distal apices 50 are not substantially pointed or acutely bent, a less invasive interface may be provided between the stent 20 and the graft 120, thereby reducing the likelihood of abrading the graft material. Similarly, since the end regions of the proximal apices 30 are not substantially pointed or acutely bent in the deployed state, a less invasive interface may be provided between the stent 20 and an inner surface of the vessel wall, thereby reducing the likelihood of damaging the vessel.

In other examples, the stent 20 may substantially overlap with the graft 120. The stent 20 may be disposed substantially internal to the graft 120 and coupled to the graft 120, for example, using sutures. In the deployed state, the barbs 60 may protrude through the graft 120 to engage tissue. In a further example, the stent 20 may be disposed substantially overlapping and external to the graft 120, in which case the barbs 60 will not perforate the graft material, but rather will directly engage tissue in the expanded state.

Many different types of graft materials may be used for the graft 120. Common examples of graft materials currently used include expandable polytetrafluoroethylene (ePTFE), polytetrafluoroethylene (PTFE), Dacron, polyester, fabrics and collagen. However, graft materials may be made from numerous other materials as well, including both synthetic polymers and natural tissues, including small intestine submucosa (SIS).

Moreover, the structure of the stent 20 also may be formed in a variety of ways to provide a suitable intraluminal support structure, and need not necessarily be provided exactly as shown in FIGS. 1, 3 and 10. Regardless of the particular overall construction of the stent, at least one apex may be provided in accordance with the examples described hereinabove. For example, the remainder of the stent may be made from a woven wire structure, a laser-cut cannula, individual interconnected rings, or any other suitable structure, and may comprise any number of struts or support members to perform the desired functions of the stent.

The stent 20 and the stent-graft 110 may be delivered into a vessel, duct, or other anatomical site using a suitable deployment system or introducer. An introducer, such as that described in PCT application WO98/53761, entitled "A Prosthesis and a Method and Means of Deploying a Prosthesis," which is incorporated herein by reference in its entirety, may be used to deploy the stent or stent-graft. PCT application WO98/53761 describes a deployment system for an endoluminal prosthesis whereby the prosthesis is radially compressed onto a delivery catheter and is covered by an outer sheath. To deploy the system, the operator slides or retracts the outer sheath over the delivery catheter, thereby exposing the prosthesis. The prosthesis expands outwardly upon removal of the sheath. The operator can directly manipulate the sheath and the delivery catheter, which provides the operator with a relatively high degree of control during the procedure. Further, such delivery devices may be compact and may have a relatively uniform, low-diameter radial profile, allowing for atraumatic access and delivery.

The delivery and deployment device used to deploy the stent 20 and the stent-graft 110 may optionally include deployment control mechanisms. For example, a proximal control mechanism may releasably retain the proximal end of the stent-graft 110 and a distal control mechanism may releasably retain the distal end of the stent-graft 110. The proximal and distal control mechanisms may comprise one or more trigger wires that releasably couple the proximal and distal ends of the stent-graft 110 to the delivery catheter. Various prosthesis retention devices, configurations, and methods of use are disclosed in PCT application WO 98/53761, previously incorporated by reference. While the above-referenced PCT application described one system for delivering and deploying the stent 20 and the stent-graft 110, other suitable delivery and deployment systems may be used to deliver a stent or stent-graft manufactured in accordance with the embodiments and techniques described hereinabove.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A stent for use in a medical procedure, the stent comprising:
    at least one apex comprising a strut having first and second generally straight portions and a curved portion disposed between the first and second generally straight portions,
    where the curved portion comprises at least one region having a cross-sectional area that is less than a respective cross-sectional area of each of the first and second generally straight portions,
    where the cross-sectional area of the curved portion is measured as being perpendicular to the strut at the at least one region of the curved portion,
    where the respective cross-sectional area of each of the first and second generally straight portions is measured as being perpendicular to the strut at the respective one of the first and second generally straight portions, and
    where the first and second generally straight portions each have a respective portion aligned with a longitudinal axis of the stent in an expanded state.

2. The stent of claim 1 further comprising a substantially uniform taper between the first generally straight portion and a midpoint of the curved portion, and a substantially uniform taper between the second generally straight portion and the midpoint, such that the midpoint comprises the smallest cross-sectional area of any point along the curved portion.

3. The stent of claim 1 further comprising a variable taper formed along at least a portion of the curved portion, the variable taper forming one or more regions along the curved portion having a reduced cross-sectional area relative to the first and second generally straight portions.

4. The stent of claim 1 where the curved portion comprises at least one arcuate segment having a cross-sectional area that is less than the respective cross-sectional area of each of the first and second generally straight portions, where the arcuate segment comprises a uniform cross-sectional area along at least a portion of its length.

5. The stent of claim 1 where the stent is coupled to at least a portion of a graft, where at least one distal apex of the stent is coupled to the graft using one or more sutures.

6. The stent of claim 1 further including at least one barb formed integrally with the stent, where the barb is formed along a transition region comprising a first straight portion of a first apex and a second straight portion of an adjacent apex.

7. The stent of claim 1 where the stent comprises multiple proximal apices and multiple distal apices,
where each proximal apex is integrally formed with a next adjacent proximal apex, and where each distal apex is integrally formed with a next adjacent distal apex,
where each of the proximal apices are circumferentially offset from the distal apices, and
where the stent comprises at least one strut segment disposed between a proximal apex and a distal apex, where the strut segment is angled with respect to the longitudinal axis of the stent in an expanded state.

8. The stent of claim 1 where the stent comprises a superelastic material, and where strains imposed upon the curved portion do not induce substantial permanent strains of the selected material.

9. A stent for use in a medical procedure, the stent comprising:
at least one apex comprising first and second generally straight portions and a curved portion disposed between the first and second generally straight portions,
where the at least one apex of the stent is in a generally arcuate expanded shape, and
where the at least one apex of the stent is configured to enter a compressed state in which at least a portion of the curved portion overlaps with itself to reduce an overall lateral width of the curved portion in the compressed state relative to the generally arcuate expanded shape.

10. The stent of claim 9 where the curved portion comprises at least one region having a cross-sectional area that is less than a respective cross-sectional area of each of the first and second generally straight portions.

11. The stent of claim 10 further comprising a substantially uniform taper between the first generally straight portion and a midpoint of the curved portion, and a substantially uniform taper between the second generally straight portion and the midpoint, such that the midpoint comprises the smallest cross-sectional area of any point along the curved portion.

12. The stent of claim 9 where the stent comprises a superelastic material, and where strains imposed upon the curved portion due to stent compression do not induce permanent strains of the selected material when the stent is in the compressed state.

13. The stent of claim 9 where the stent is coupled to at least a portion of a graft, where at least one distal apex of the stent is coupled to the graft using one or more sutures.

14. The stent of claim 9 where the stent comprises multiple proximal apices and multiple distal apices,
where each proximal apex is integrally formed with a next adjacent proximal apex, and where each distal apex is integrally formed with a next adjacent distal apex,
where each of the proximal apices are circumferentially offset from the distal apices, and
where the stent comprises at least one strut segment disposed between a proximal apex and a distal apex, where the strut segment is angled with respect to a longitudinal axis of the stent in an expanded state.

15. A stent having proximal and distal ends, the stent comprising:
a series of proximal apices disposed at the proximal end of the stent, where each proximal apex comprises a first strut having a first generally straight portion, a second generally straight portion, and a curved portion disposed between the first and second generally straight portions, where the curved portions of the proximal apices each comprise at least one region having a cross-sectional area that is less than a respective cross-sectional area of each of the respective first and second generally straight portions;
a series of distal apices disposed at the distal end of the stent, where each distal apex comprises a second strut having a first generally straight portion, a second generally straight portion, and a curved portion disposed between the first and second generally straight portions, where the curved portions of the distal apices each comprise at least one region having a cross-sectional area that is less than a respective cross-sectional area of each of the respective first and second generally straight portions; and
at least one strut segment disposed between a proximal apex and a distal apex,
where each of the proximal apices are circumferentially offset from the distal apices in an expanded state,
where the cross-sectional area of the curved portion of each of the proximal apices is measured as being perpendicular to the first strut at the at least one region of the curved portion,
where the cross-sectional area of each of the first and second generally straight portions of each of the proximal apices is measured as being perpendicular to the respective first strut at the respective one of the first and second generally straight portions, and
where the first and second generally straight portions of each of the proximal apices each have a respective portion aligned with a longitudinal axis of the stent in an expanded state.

16. The stent of claim 15 where the stent is coupled to at least a portion of a graft, where at least one distal apex of the stent is coupled to the graft using one or more sutures.

17. The stent of claim 15 where each proximal apex is integrally formed with a next adjacent proximal apex, and where each distal apex is integrally formed with a next adjacent distal apex.

18. The stent of claim 15 where the at least one strut segment is angled with respect to a longitudinal axis of the stent in an expanded state.

19. The stent of claim 18 where the at least one strut segment is substantially parallel to the longitudinal axis of the stent in a compressed state.

20. The stent of claim 15 further including at least one barb formed integrally with the stent, where the barb is formed along a transition region comprising the first generally straight portion of a first proximal apex and the second generally straight portion of a second proximal apex, where the first proximal apex and the second proximal apex are adjacent to one another.

* * * * *